(12) United States Patent
Seiwatz et al.

(10) Patent No.: US 6,268,602 B1
(45) Date of Patent: *Jul. 31, 2001

(54) METHOD FOR MANUFACTURING CALIBRATED RADIATION DOSIMETER

(75) Inventors: Henry Seiwatz, Wayne, NJ (US); Carl A. Listl, New Hyde Park, NY (US); J. Michael Donahue, Oakland, NJ (US); David F. Lewis, Monroe, CT (US)

(73) Assignee: ISP Investments Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/013,828

(22) Filed: Jan. 27, 1998

Related U.S. Application Data

(63) Continuation-in-part of application No. 08/554,540, filed on Nov. 7, 1995, now Pat. No. 5,637,876.

(51) Int. Cl.[7] .................................................. G01J 1/02
(52) U.S. Cl. ................................ 250/252.1; 250/473.1; 250/474.1
(58) Field of Search .......................... 250/252.1, 473.1, 250/474.1, 475.2

(56) References Cited

U.S. PATENT DOCUMENTS 4,507,226 * 3/1985 Noakes et al. ..................... 252/600
5,206,118 * 4/1993 Sidney et al. ...................... 430/343

OTHER PUBLICATIONS

Bushong, S. "Radiological Science for Technologists . . . " Mosby Co. St. Louis, p. 230 (1980).*

Pratt, W., *Digital Image Processing*, John Wiley & Son (1978) pp. 356–357.*

* cited by examiner

*Primary Examiner*—Georgia Epps
*Assistant Examiner*—Richard Hanig
(74) *Attorney, Agent, or Firm*—William J. Davis; Jules E. Goldberg

(57) ABSTRACT

In a method for manufacturing a calibrated radiation dosimeter, a layer of radiation sensitive material is applied to a substrate, the radiation sensitive material having an optical density which varies in accordance with a degree of radiation exposure. A pre-exposure optical density of the layer of radiation sensitive material is optically measured and subsequently the layer of radiation sensitive material is exposed to a known dose of radiation. Thereafter, a post-exposure optical density of the layer of radiation sensitive material is optically measured. Using at least the pre-exposure optical density, the post-exposure optical density, and the known dose of radiation, one computes mathematical parameters defining a predetermined mathematical function. The computed mathematical parameters are applied in encoded form to the substrate (e.g., printed in bar code form on the substrate or a holder card).

7 Claims, 3 Drawing Sheets

METHOD FOR MANUFACTURING CALIBRATED RADIATION DOSIMETER

CROSS-REFERENCE TO RELATED APPLICATION

This application is a continuation-in-part of application Ser. No. 08/554,540 filed Nov. 7, 1995 now U.S. Pat. No. 5,637,876.

BACKGROUND OF THE INVENTION

This invention relates to a radiation dosimeter. More particularly, this invention relates to a method for manufacturing a radiation dosimeter. Even more particularly, this invention relates to a manufacturing method wherein radiation sensitive patches of radiation dosimeters are individually calibrated for sensitivity to facilitate eventual use in quantitatively measuring radiation doses.

In facilities where radioactive materials are used, for example, in hospitals where cancer patients receive radiation treatments or in blood banks where blood products are irradiated, various methods are used to quantitatively determine the radiation dose. The methods practiced include the use of thermoluminescent dosimeters (TLD's), ionization-type radiation detectors, photographic film, and radiochromic materials. TLD's are inconvenient because they require a complicated and time-consuming read-out process. Ionization-type radiation detectors are awkward and unwieldy and require a complicated setup. Photographic film requires a time-consuming chemical processing procedure before read-out. Radiochromic materials are inconvenient in current practice because the calculation of the dose requires a complex sequence of steps, subject to operator error.

U.S. Pat. No. 5,637,876 describes a radiation dosimeter, exemplarily for use in determining a level of radiation to which a patient is subjected during radiation treatment, which comprises a substrate provided with a layer of radiation sensitive material. The radiation sensitive material has an optical density which varies systematically in accordance with the degree of radiation exposure. In addition, the substrate is provided with optically readable coding which identifies encoded mathematical parameters for enabling an automated calculation of dosage from a detected post-exposure optical density (or change in optical density) of the radiation sensitive material. Where the post-exposure optical density varies as a linear function of the amount of radiation exposure, the mathematical parameters include a slope parameter and a y-intercept parameter.

According to U.S. Pat. No. 5,637,876, the dosimeter may take the form of a card or a flexible substrate which is positionable on the patient or other irradiation subject and which is also positionable in, or slidable through a slot in, a dose reader, described below. Preferably, the coding on the substrate takes the form of a bar code. In that case, the coding and the optical density of the exposed layer of radiation sensitive material may be read by the same dose reader instrument. The bar coding and the reflection (or transmission) intensity of the radiation sensitive layer may be sensed during a sliding of the dosimeter through a slot on the dose reader instrument. Alternatively, movable optical elements may be provided for reading the bar code information and measuring the optical density of the radiation sensitive layer while the dosimeter is held in a slot or recess on the dose reader instrument.

Also described in U.S. Pat. No. 5,637,876 is a dose reader instrument which is used with the dosimeter in measuring a radiation level to which a patient or other object is subjected and which comprises an optical sensor for sensing a range of variable optical densities of a radiation sensitive layer. The sensor includes or is connected to measurement componentry for determining an optical density of the layer of radiation sensitive material on the substrate. The dose reader further comprises a decoder operatively connected to the optical sensor for decoding the mathematical parameters encoded in the optically readable coding on the substrate. A computer is operatively connected to the measurement componentry and the decoder for computing, according to a predetermined mathematical function including the parameters determined from the coding on the substrate by the decoder, a quantitative radiation dose to which the layer of radiation sensitive material was exposed. A display or other communicating component (such as speech synthesis circuitry) is operatively connected to the computer for communicating the computed quantitative radiation dose to an operator.

As discussed above with respect to the structure of the dosimeter, where the radiation level to which a subject is exposed is linearly related to the change in the optical density of the exposed layer of radiation sensitive material, the mathematical parameters encoded on the dosimeter include a slope parameter and a y-intercept parameter. The predetermined mathematical function used in computing the level of radiation exposure is $[\log[I(0)-D]-\log[I(s)-D]-b]/m$ where D is a premeasured background intensity determined for the instrument during production and assembly, m is the slope parameter, b is the y-intercept parameter, $I(0)$ is a sensed pre-exposure reflection or transmission intensity of the layer of radiation sensitive material, $I(s)$ is a sensed post-exposure reflection or transmission intensity of the layer of radiation sensitive material, and $[\log[I(0)-D]-\log[I(s)-D]]$ is a measured optical density change in the layer of radiation sensitive material.

Where another mathematical function describes the relationship between post-exposure optical density change of a radiation sensitive dosimeter layer and the degree of irradiation, different mathematical parameters are encoded on the dosimeter, e.g., in a bar code. The principle underlying the invention of U.S. Pat. No. 5,637,876 is that the calibration information pertaining to the relationship between a post-exposure optical density change of a radiation sensitive dosimeter layer and the degree of irradiation is encoded on the dosimeter itself, thereby enabling automatic computation of the radiation dosage from a measured optical density change.

Pursuant to the disclosure of U.S. Pat. No. 5,637,876, a method for determining a level of exposure to radiation utilizing the radiation dosimeter and dose reader instrument described above comprises the step of optically measuring the pre-exposure optical density of the layer of radiation sensitive material. In addition, the coding on the dosimeter substrate is scanned to automatically determine the encoded mathematical parameters. Generally, after measurement of the pre-exposure optical density of the radiation sensitive layer, the dosimeter is placed on a subject to be irradiated. The method further comprises the steps of then exposing the radiation sensitive layer (and the subject) to radiation and subsequently optically measuring a post-exposure optical density of the radiation sensitive layer. Then, from the pre-exposure optical density, the post-exposure optical density, and the mathematical parameters and in accordance with a predetermined mathematical algorithm, a quantitative radiation dose to which the layer of radiation sensitive material was exposed is automatically computed. Preferably, the computed quantitative radiation dose is automatically indicated on a display.

The optical density of the layer of radiation sensitive material may be measured by sensing a reflection (or transmission) intensity of the layer. The optical density is related logarithmically to the sensed reflection (or transmission) intensity. Where the reflection intensity is sensed, a reflection densitometer may be used.

In practice, the calibration information (e.g., the y-intercept and the slope) printed on any particular dosimeter represents, at best, an average sensitivity for an entire lot of radiation sensitive dosimeter material of which the particular dosimeter is a part. Calibration information is currently derived, in a proprietary process, by exposing samples of a production batch of dosimeter material (radiation sensitive layers) to known levels of radiation, calculating their specific responses (density changes per known doses), and computing an average of the specific responses. The average values are printed in code on each dosimeter of the production batch.

Of course, manufacturing tolerances in this calibration process give rise to variances in accuracy of the calibration information printed on the individual dosimeters. The variance of the sensitivity of individual film chips within a lot results in a limitation on the accuracy of radiation dose measurements made with the individual film chips.

SUMMARY OF THE INVENTION

An object of the present invention is to provide an improved method for manufacturing radiation dosimeters of the type described in U.S. Pat. No. 5,637,876.

A more specific object of the present invention is provide a method for manufacturing calibrated dosimeters of the type described in U.S. Pat. No. 5,637,876.

A dosimeter of the above-described type, and particularly the layer of radiation sensitive material thereof is a kind of sensor which has an irreversible reaction when subjected to an action such as electromagnetic (X-ray, gamma ray) energy. The reaction is progressive, i.e., varies with the amount of the action to which the sensor is subjected. In addition, the reaction is cumulative, i.e., exhibits a total reaction which is a function of the sum of all the actions to which the sensor is subjected. Moreover, it is to be recognized that the dosimeters of the above-described type are not necessarily disabled from reacting to further action after being subjected to one or more initial actions. In dosimeters used in the method of U.S. Pat. No. 5,637,876, a general mathematical function which describes the relationship between the action and the reaction is known. The calibration process serves to determine specific constants of the mathematical function.

Pursuant to the above observations, a general object of the present invention is to provide a method for manufacturing calibrated sensors of the type which have an irreversible reaction when subjected to an action (e.g., energy), wherein the reaction is progressive and cumulative and related by a known generic mathematical function to the action.

In a method for manufacturing an individually calibrated dosimeter in accordance with the present invention, a layer of radiation sensitive material is applied to a substrate, the radiation sensitive material having an optical density which varies in accordance with a degree of radiation exposure. A pre-exposure optical density of the layer of radiation sensitive material is optically measured and subsequently the layer of radiation sensitive material is exposed to a known dose of radiation. Thereafter, a post-exposure optical density of the layer of radiation sensitive material is optically measured. Using at least the pre-exposure optical density, the post-exposure optical density, and the known dose of radiation, one computes mathematical parameters defining a predetermined mathematical function. The computed mathematical parameters are applied in encoded form to the substrate (e.g., printed in bar code form on the substrate or a holder card).

In accordance with a preferred embodiment of the present invention, many, if not all, of the steps in the manufacturing process are performed automatically. Specifically, the optical measuring of the pre- and post-exposure optical densities of the layer of radiation sensitive material and the computing of the calibration parameters are performed automatically. In addition, the computed mathematical parameters may be reduced automatically to encoded form and applied automatically to (e.g., printed on) the substrate. Also, the pre-exposure optical density is automatically stored in electronically encoded form and subsequently automatically retrieved to compute the mathematical parameters.

Preferably, the mathematical parameters are encoded in optically readable form such as in bar codes.

In accordance with another feature of the present invention, the manufacturing method further comprises the step of automatically generating an identification code for the substrate, to distinguish the substrate from other substantially similar substrates under manufacture. The identification code facilitates or enables a computerized, assembly-line manufacturing operation by enabling the association of the proper pre-exposure and post-exposure optical densities.

As described in prior U.S. Pat. No. 5,637,876, the pre-exposure optical density and the post-exposure optical density of the layer of radiation sensitive material may be measured by operating a reflection densitometer apparatus to sense a reflection intensity.

The substrate is preferably provided with optically readable coding uniquely identifying the respective dosimeter.

As discussed above, the mathematical function may be a linear function, so that the calibration parameters include a slope parameter and a y-intercept parameter. According to a more specific feature of the present invention, measuring the pre-exposure optical density includes the step of sensing a pre-exposure reflection or transmission intensity of the layer of radiation sensitive material, the step of measuring the post-exposure optical density including the step of sensing a post-exposure reflection or transmission intensity of the layer of radiation sensitive material. The predetermined mathematical function is $E_r=[\log[I(0)-D]-\log[I(s)-D]-b]/m$ where $E_r$ is the known radiation dose, D is a premeasured background intensity, m is a slope parameter included in the mathematical parameters, b is a y-intercept parameter included in the mathematical parameters, $I(0)$ is the sensed pre-exposure reflection or transmission intensity, and $I(s)$ is the sensed post-exposure reflection or transmission intensity.

A manufacturing method in accordance with the present invention produces radiation dosimeters used to make dose measurements whose accuracy depends only on the accuracy of dosimeters used to make dose measurements whose accuracy depends only on the accuracy of the calibration and not on the uniformity of the radiation sensitive material in a manufacturing lot or batch. Accordingly, dosimetry errors are eliminated which would normally be caused by variations in the radiation sensitivity of individual patches because of manufacturing tolerances.

In a dosimeter manufacturing method in accordance with the present invention, production quality standards may be relaxed without affecting system performance. This results in less waste and lower costs. A dosimeter manufacturing method in accordance with the present invention provides the potential for producing high-accuracy dosimeters routinely at low cost.

The present invention, in accordance with a more general conceptualization thereof, is directed to a method for calibrating a sensor which has an irreversible reaction when subjected to an action, wherein the reaction is progressive and cumulative and related by a known generic mathematical function to the action. This generalized method comprises the steps of subjecting the sensor to a plurality of incremental instances of the action to which the sensor is sensitive, each of the incremental instances of the action having a known magnitude, measuring a cumulative reaction of the sensor to a respectively accumulated amount of the action after each time the sensor is subjected to an instance of the action, and computing the unknown parameters, in accordance with the mathematical function, from the known magnitudes of the incremental instances and from the measured cumulative reactions of the sensor.

The action may take the form of a specific kind of energy such as electromagnetic radiation and more specifically X-rays or gamma rays. The cumulative reaction in this case is a change in optical density of the sensor. Concomitantly, the measuring of the cumulative reaction includes optically measuring the change in optical density of the sensor.

Pursuant to another feature of the present invention, the number of incremental instances of the action is equal to the total number of unknown parameters of the known mathematical function.

DETAILED DESCRIPTION

Figure 1:
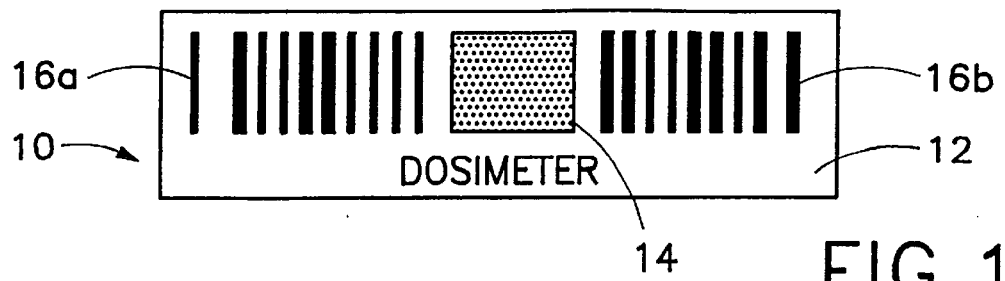
FIG. 1 is a plan view of a dosimeter or radiation measurement patch manufactured in accordance with the present invention.

As illustrated in FIG. 1, a radiation dosimeter 10 comprises a planar substrate or carrier 12 which can be positioned on a patient or other person or object to which radiation is applied. Dosimeter 10 is used, as discussed in detail hereinafter, for determining a level of radiation to which a patient, person or object is subjected during a radiation treatment procedure. Substrate 12 is provided with a patch or layer 14 of radiation sensitive material. The radiation sensitive material has an optical density which varies systematically, e.g., linearly, in accordance with the amount of radiation exposure. In addition, substrate 12 is provided with one or more optically readable bar codes 16a, 16b which identify encoded mathematical parameters, particularly a slope and an intercept of a linear equation or expression. These encoded mathematical parameters enable an automated calibration of the sensitivity of the particular radiation sensitive patch or layer 14 of dosimeter 10 and concomitantly enable an automated calculation of radiation dosage from a detected change in optical density of the radiation sensitive material of patch 14.

Although FIG. 1 shows two bar codes 16a and 16b, it may be preferable, for example, for space reasons, to provide a single bar code, i.e., a single series of bars of varying widths. Moreover, the bar coding 16a, 16b on substrate 12 may include a unique identification of the respective dosimeter, enabling a seriatim measurement of several pre-exposure optical densities and storage of the measured densities in memory for later selective recall. This option is particularly useful where several dosimeters 10 are applied to the same subject and exposed during the same irradiation process.

Figure 2:
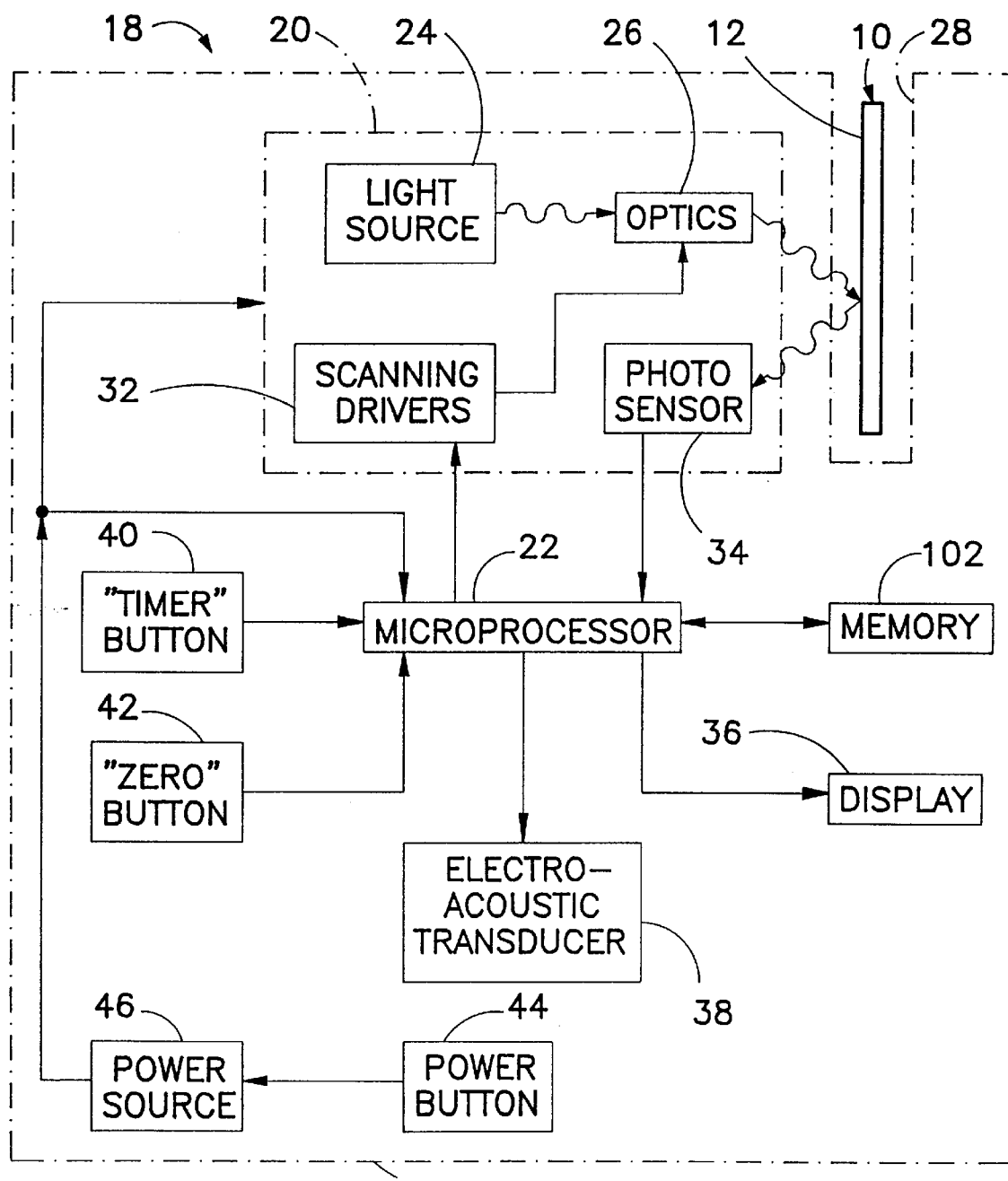
FIG. 2 is a block diagram of a dose reader used to determine a radiation dosage received by the dosimeter of FIG. 1.

Prior to and after exposure of patch 14 to radiation, the optical density of the radiation sensitive material of the patch is measured by a dose reader 18, illustrated diagrammatically in FIG. 2. Dose reader 18 comprises an optical scanner or reflection densitometer 20 for sensing a range of variable reflection intensities at a multiplicity of different locations on substrate 12. The optical scanner or scanning reflection densitometer 20 cofunctions with a microprocessor 22 to determine or measure an optical density of radiation sensitive patch 14 and to decode the mathematical parameters encoded in bar codes 16a and 16b. A measured optical density is logarithmically related to a sensed reflection intensity, as indicated in greater detail hereinafter.

Optical scanner or scanning reflection densitometer 20 includes a light source 24 which produces electromagnetic radiation of a predetermined intensity and range of wavelengths. The electromagnetic radiation from light source 24 is directed by optical elements 26 to dosimeter 10, which is held in a slot 28 in a frame or casing 30. Optical elements 26 are controlled by scanning drivers 32 in turn controlled by microprocessor 22. Optical scanner or scanning reflection densitometer 20 further includes a photocell or optical sensor element 34 for detecting radiation reflected from dosimeter 10. Photocell 34 is operatively connected to microprocessor 22 for feeding thereto an electrical signal identifying the intensity of the reflection from different points on dosimeter 10.

In accordance with the signal from photocell 34, microprocessor 22 acts to determine the optical density of radiation sensitive patch 14 and to decode the parametric information encoded in bar codes 16a and 16b. As discussed in detail hereinafter, microprocessor 22 also functions to compute a quantitative value for a radiation dose from the decoded parameters and the measured optical density of radiation sensitive patch 14, both before and after exposure to radiation.

As further illustrated in FIG. 2, dose reader 18 further includes a display 36 or other communicating component (such as speech synthesis circuitry—not illustrated) which is operatively connected to microprocessor 22 for communicating the computed quantitative radiation dose to an operator. Dose reader 18 additionally includes an electroacoustic transducer or speaker component 38 connected to an output of microprocessor 22 for generating an alert sound in response to a signal from the microprocessor.

A "timer" button 40 and a "zero" button 42 provided on frame 30 are connected to microprocessor 22 for inducing a counting operation and a pre-exposure optical density measurement operation by the microprocessor, respectively. More specifically, timer button 40 is operatively coupled to microprocessor 22 for enabling the post-exposure optical density measurement and computation of the quantitative radiation dose only upon the lapse of a known or predetermined fixed interval after exposure of the layer of radiation sensitive material to radiation.

The radiation level to which a subject is exposed is systematically, e.g., linearly, related to the change in optical density of the exposed radiation sensitive patch 14. A predetermined linear mathematical function used by microprocessor 22 in computing the level of radiation exposure is $[\log[I(0)-D]-\log[I(s)-D]-b]/m$ where D is a premeasured background intensity determined for a particular dose reader 18 during production and assembly, m is the slope parameter encoded in bar code 16a or 16b, b is the y-intercept parameter encoded in bar code 16b or 16a, I(0) is a sensed pre-exposure reflection intensity of radiation sensitive patch 14, and I(s) is a sensed post-exposure reflection intensity of patch 14, and $[\log[I(0)-D]-\log[I(s)-D]]$ is a measured optical density change of patch 14.

As additionally illustrated in FIG. 2, dose reader 18 includes a power button 44 on frame 30. Power button 44 induces the supply of power from a source 46 to various components of the dose reader, including microprocessor 22 and optical scanner or scanning reflection densitometer 20.

Figure 3:
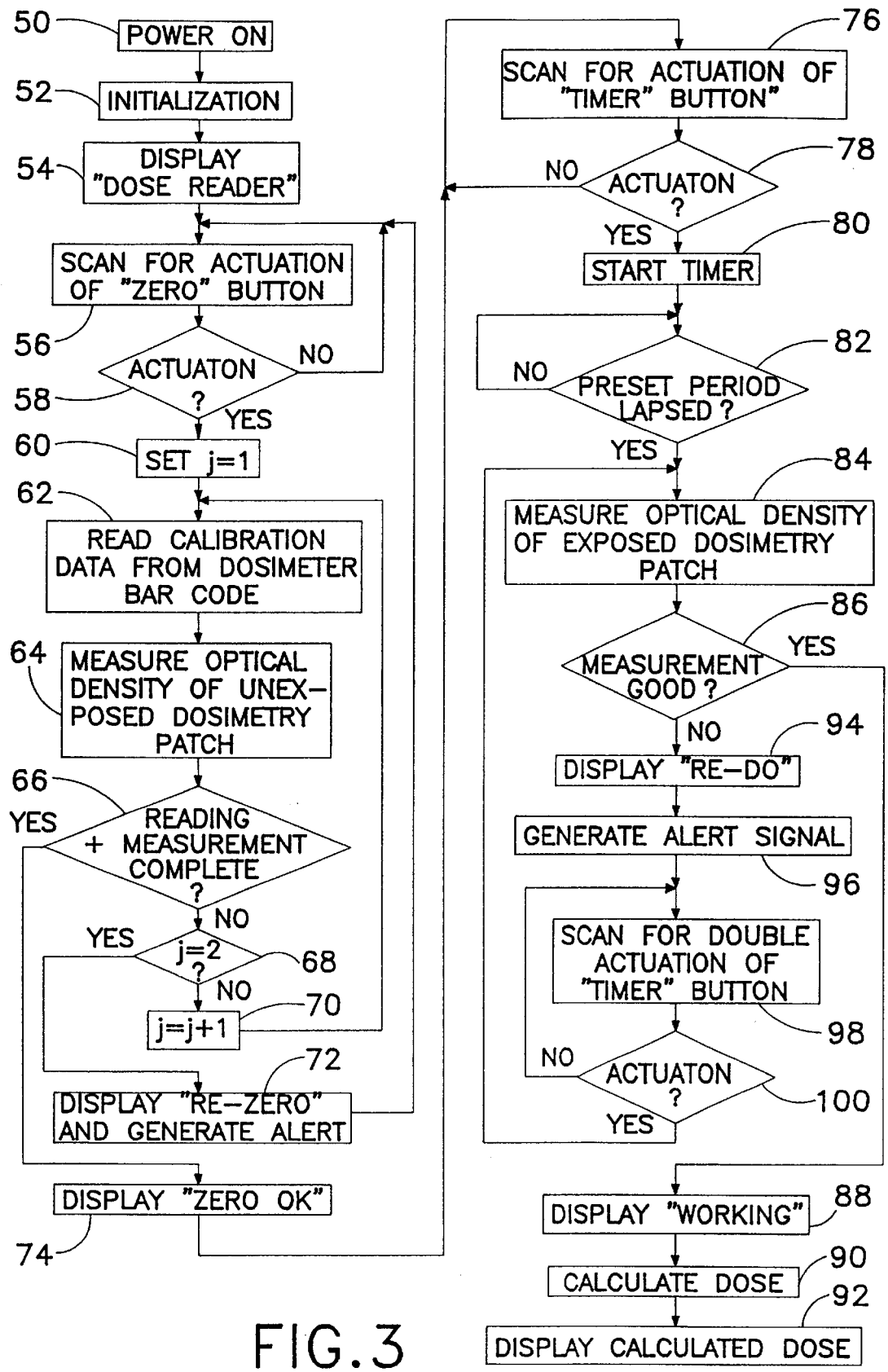
FIG. 3 is a flow chart diagram showing steps in the operation of a microprocessor included in the dose reader of FIG. 2.

FIG. 3 diagrammatically depicts a dosimetry method as controlled by microprocessor 22. Upon a receiving a signal from power button 44 in a step 50, microprocessor 22 undergoes a self-initialization sequence 52 and subsequently energizes display 36, in a step 54, to show the words "Dose Reader." Microprocessor 22 then undertakes a scan 56 to determine whether "zero" button 42 has been actuated. Upon determining at a decision junction 58 that "zero" button 42 has been pressed, microprocessor 22 allots a value of 1 to a temporary parameter j in a step 60 and then cooperates with optical scanner or scanning reflection densitometer 20 in a step 62 to read the calibration data (m, b) for a particular dosimeter 10 from the bar codes 16a and 16b thereon. In addition, microprocessor 22 coacts with optical scanner or scanning reflection densitometer 20 in a step 64 to sense a pre-exposure reflection intensity and calculate a corresponding pre-exposure optical density of radiation sensitive patch 14. Of course, the unexposed densitometer 10 has been inserted into (or slid through) slot 28 prior to (or during) the scanning of the densitometer by optical scanner or scanning reflection densitometer 20.

Upon determining at a decision junction 66 that reading and measurement steps 62 and 64 have not been successfully completed, microprocessor 22 inquires at 68 whether temporary parameter j is equal to 2. If not, parameter j is incremented in a step 70 and microprocessor 22 again undertakes reading and measurement steps 62 and 64. If microprocessor 22 has already made two attempts at reading bar codes 16a and 16b and measuring the optical density of radiation sensitive patch 14, the microprocessor energizes display 36 to show the word "Re-Zero" and generates an audible alert signal via electroacoustic transducer 38 (step 72). Dose reader 18 may also be provided with an additional visual indicator such as a red light (not shown) for alerting a user that dose reader 18 is unable to calibrate or read a dosimeter 10 in slot 28. The dosimeter 10 may be reinserted or another dosimeter card may be tried.

Once microprocessor 22 determines the particular calibration parameters m and b from bar codes 16a and 16b on dosimeter 10, as ascertained at decision junction 66, the microprocessor activates display 36 to display the term "Zero OK" in a step 74 and then scans, in a step 76, for an actuation of timer button 40. An actuation of button 40 means that dosimeter 10 has been removed from slot 28, placed on a subject and irradiated. The user should press button 40 as soon as irradiation has ceased. The user then places the exposed dosimeter 10 back into slot 28.

Upon an actuation of "timer" button 40, detected by microprocessor 22 in an inquiry 78, the microprocessor starts an internal clock running in a step 80. After the passage of a pre-established interval or period of time, monitored by microprocessor 22 in an inquiry 82, the microprocessor coacts with optical scanner or scanning reflection densitometer 20 in a step 84 to measure the optical density of the exposed radiation sensitive patch 14. If the measurement is good, as determined by microprocessor 22 at a decision junction 86, the microprocessor activates display 36 in a step 88, calculates the radiation dose in a step 90 and finally displays the calculated dosage in a step 92. As discussed above, microprocessor 22 computes the level of radiation exposure from the equation or expression $[\log[I(0)-D]-\log[I(s)-D]-b]/m$ where D is a premeasured background intensity determined for a particular dose reader 18 during production and assembly, m is the slope parameter encoded in bar code 16a or 16b, b is the y-intercept parameter encoded in bar code 16a or 16b, I(0) is a sensed pre-exposure reflection intensity detected in step 64, and I(s) is a sensed post-exposure reflection intensity detected in step 84, while $[\log[I(0)-D]-\log[I(s)-D]]$ is an optical density change in the layer of radiation sensitive material.

If the measurement of the post-exposure optical density of radiation sensitive patch 14 is unsatisfactory, as determined at decision junction 86, microprocessor 22 energizes display 36 in a step 94 to show the word "Re-do" and energizes electroacoustic transducer 38 in a step 96 to issue an audible alert signal. The microprocessor then waits for a double actuation of timer button 40 (step 98). If the timer button is pressed twice, as determined at 100, microprocessor 22 undertakes immediately another measurement of the optical density of the exposed radiation sensitive patch 14 of the dosimeter 10 in slot 28.

In performing a dosimetry procedure using dosimeter 10 and dose reader 18, the reflectivity of radiation sensitive patch 14 is optically measured prior to exposure thereof to radiation to thereby determine a pre-exposure optical density of patch 14. In addition, bar codes 16a and 16b on dosimeter substrate 12 are scanned to automatically determine the encoded mathematical parameters m and b. Subsequently, after exposure of the dosimeter to radiation and upon lapse of a preset period after the exposure, the post-exposure optical density of radiation sensitive patch 14 is measured optically. Then, in accordance with a predetermined mathematical algorithm incorporating the pre-exposure optical density, the post-exposure optical density, and the decoded or read mathematical parameters m and b, microprocessor 22 automatically computes a quantitative value of the radiation dose to which a subject and the dosimeter 10 were exposed. The computed dose is automatically displayed in virtual real time, i.e., shortly after the irradiation procedure.

The greatest accuracy is obtained by waiting a predetermined period after the termination of an irradiation procedure before measuring the optical density of the exposed patch 14. The radiation sensitive material of patch 14 is well known in the industry.

Preferably, the reading of bar codes 16a and 16b is performed prior to exposure of the dosimeter 10 to radiation. However, the scanning of the parametric codes 16a and 16b and the associated determination of the mathematical parameters m and b may be implemented later, for example, at the time the post-exposure optical density of radiation sensitive patch 14 undertaken.

In an alternative dosimetry method, reflection densitometer 20 (FIG. 2) is a simple densitometer, without the scanning capability provided by scanning drivers 32 and adjustable optics 26. Thus, in dose reader 18, scanning drivers 32 may be omitted. To enable reflection densitometer 20 to sense bar coding 16a and 16b for a determination of mathematical parameters m, b, a user simply slides dosimeter 10 through slot 28, in the same manner that one slides, for example, a credit card through a slot past a magnetic reader. The measurement of the optical density of patch or layer 14 may be made during the same swiping motion of the dosimeter 10. Alternatively, dosimeter 10 may be temporarily left in slot 28 during the measurement of optical density.

It is to be noted that the dosimetry method and dose reader 18 may be modified to enable measurement of the post-exposure optical density of radiation sensitive patch 14 at different times after irradiation has ceased. For example, where the function $[\log[I(0)-D]-\log[I(s)-D]-b]/m$ is used to calculate the radiation dose from a post-exposure reflection intensity measured a predetermined interval after exposure, the result computed from this expression may be automatically adjusted by microprocessor 22 (FIG. 2) to derive the actual radiation dose when the post-exposure reflection intensity is measured at a different time, i.e., before or after the predetermined post-exposure interval has elapsed. Accordingly, timer button 40 may be used to start a clock internal to microprocessor 22 by which the microprocessor measures the time from the cessation of irradiation to the measurement of optical density. The difference between the measured interval and the preset time period determines a modification amount or adjustment factor to be applied to the calculated radiation dose to derive a final actual radiation dose. To that end, microprocessor 22 is connected to a memory 102 provided in dose reader 18 for storing a table of modification amounts or adjustment factors.

It is advantageous if bar coding 16a, 16b on substrate 12 includes a unique identification of the respective dosimeter 10. This enables, for instance, the utilization of several dosimeters on the same subject during the same irradiation procedure. The pre-exposure optical densities of the radiation sensitive patches 14 of the respective dosimeters 10 are measured in seriatim and stored by microprocessor 22 in memory 102. Later, upon the sliding of a particular exposed dosimeter 10 through slot 28 and the measurement of the post-exposure optical density of that dosimeter, microprocessor 22 accesses memory 102 and retrieves the respective pre-exposure optical density for use in computing the radiation dose experienced by the particular dosimeter 10. Generally, the measured pre-exposure densities are automatically stored by microprocessor 22 in association with the dosimeter identities read from coding 16a, 16b. Addresses in memory 102 for the measured pre-exposure densities may be determined by the dosimeter identities. Alternatively, both the measured pre-exposure densities and the respective dosimeter identities may be stored at the same locations. Of course, when only one dose reader is available for making multiple dose measurements pursuant to this procedure, the above-described table of modification amounts or adjustment factors is necessary.

Figure 4:
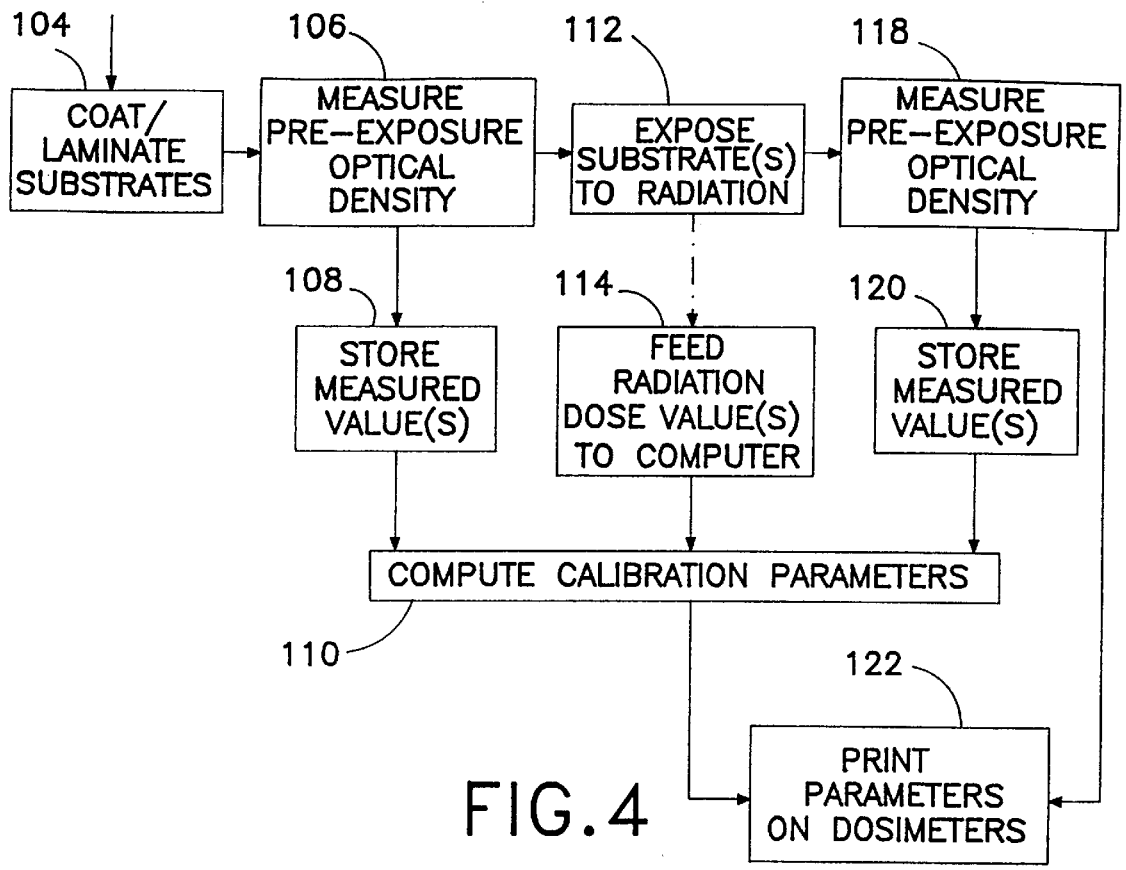
FIG. 4 is a block diagram showing steps in a method for manufacturing an individually calibrated dosimeter, in accordance with the present invention.

As illustrated in FIG. 4, a calibrated dosimeter as described hereinabove with reference to FIG. 1 is manufactured by initially applying a layer of radiation sensitive material to a substrate in a step 104, the radiation sensitive material having an optical density which varies in accordance with a degree of radiation exposure. In a subsequent step 106, a pre-exposure optical density of the layer of radiation sensitive material is optically measured. The measured optical density value is stored in a step 108 for later use in a computation step 110.

After the pre-exposure optical density is measured (step 106), the layer of radiation sensitive material is exposed to a known dose of radiation in step 112. This exposure step may be implemented by transporting a roll of patches to a gamma radiation facility, for example, one operated under the auspices of NIST. The roll of patches is placed perpendicular to the gamma flux and the roll is radiated from both sides. Other refinements may be taken to ensure the uniformity of the irradiation and minimize set-up time. These refinements include providing electron equilibration plates on each side of the roll, irradiating from both sides of the roll, rotating the roll on axis during the irradiation, providing a precise small angle off-set from the perpendicular, and measuring the uniformity of the dose on both sides of the roll with a calibrated dosimeter. Since a roll typically contains about 10,000 patches, the cost of a calibration irradiation is likely to be no more than a few cents per patch. The radiation dose is fed in a step 114 to a computer 116 (FIG. 5) for use in the computation of the calibration parameters in step 110.

After the patches have been exposed to a known radiation dose in step 112, the post-exposure optical densities of the patches are measured in a step 118 and temporarily stored in a step 120. Using the pre-exposure optical density stored in step 108, the post-exposure optical densities stored in step 120, and the known dose of radiation received in step 114, computer 116 (FIG. 5) computes y-intercept b and slope m for each patch in the roll. The computed parameters are applied in encoded form to the respective substrates in step 122. More specifically, the computed y-intercept b and slope m for each patch are printed in bar code form on the respective patches, dosimeters, substrates or holder cards.

Figure 5:
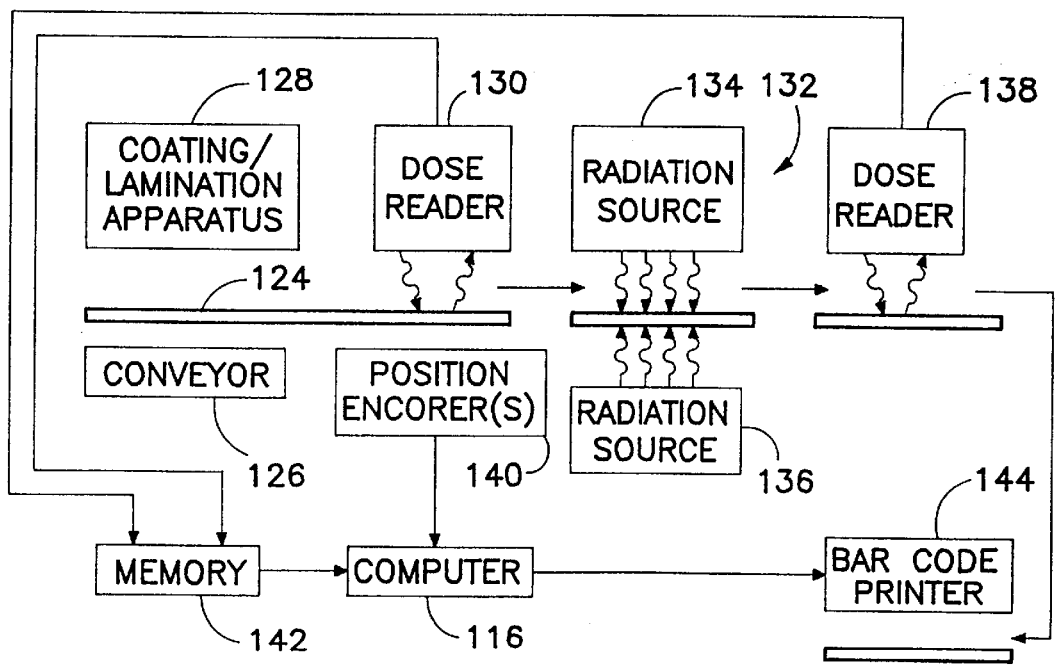
FIG. 5 is a block diagram of an assembly for performing the method illustrated diagrammatically in FIG. 4.

FIG. 5 schematically illustrates a facility for assembly line manufacture of individually calibrated dosimeters 10. A sheet or web 124 is fed by a conveyor 126 to a laminating apparatus 128 wherein a preselected number of coatings of radiation sensitive material such as pentacosadiynoic acid, having predetermined thicknesses, are applied to the sheet 124. Sheet 124 may be wound into a roll (not shown) and transported to a dose reader 130 operationally similar to dose reader 18 described above. Dose reader 130 may include a camera with the same light source and the same optical characteristics as dose reader 18. Dose reader 18 and/or 130 may be a transmission densitometer, which facilitates the use of mirrors to transmit the same measurement beam a plurality of times through a patch, thereby enhancing the sensitivity of the measurement process.

At dose reader 130, the roll of patches or dosimeter substrates is advanced one patch width at a time from an initial starting position into the dose reader 130. Patch sheet 124 is then wound about a take-up roll (not shown) for delivery to a calibration exposure station 132 having one or two high-intensity X-ray units 134 and 136 with ionization type integrating dose rate meters. The integrated dose readout is used to de-activate the X-ray tubes when a preset dose has been reached. The true level of this preset dose level must be calibrated periodically by reference to a secondary standard calibrated by NIST. The correlation between X-rays and gamma rays should be good because the spatial nature of the radiation patterns is similar. Higher accuracy is achievable with the method described above with reference to FIG. 4: pre-exposing the patches in bulk roll form to high energy gamma rays at NIST.

After irradiation at station 132, the film sheet 124 is conveyed to another dose reader 138 (possibly the same as device 130, used to perform the pre-exposure optical density measurements). Dose reader 138 is operated to optically measure the post-exposure optical densities of the individual patches or sensor elements in sheet 124. One or more position encoders 140 cooperate with computer 116 in tracking or identifying the individual patches or sensor elements in sheet 124. Position encoders 140 and computer 116 may assign identification codes such as serial numbers to the individual patches or sensor elements in sheet 124. The identification codes may be used to designate storage cells in a digital memory 142 which is operatively connected at inputs to dose readers 130 and 138 and at an output to computer 116. Memory 142 may also store the radiation dose applied at station 132.

As discussed above, total radiation exposure for a radiation sensitive layer or patch 14 of dosimeter 10 is linearly related to the optical density of the layer or patch 14. Accordingly, computer 116 is programmed to calculate, as the calibration parameters, a slope and a y-intercept. More specifically, computer 116 uses the mathematical function $E_r=[\log[I(0)-D]-\log[I(s)-D]-b]/m$ where $E_r$ is the known radiation dose, D is a premeasured background intensity, m is the slope parameter and b is the y-intercept parameter to be computed, I(0) is the sensed pre-exposure reflection or transmission intensity, and I(s) is the sensed post-exposure reflection or transmission intensity.

As further illustrated in FIG. 5, a bar code printer 144 is connected to computer 116 and disposed downstream of dose reader 138 for providing each dosimeter 10 with a bar code specifying the respective y-intercept and slope parameters of the dosimeter's linear radiation sensitivity function. The dosimeter patches are indexed one patch width at a time through the printer 144, under the control of computer 116 acting in response to signals from encoders 140.

As disclosed above, many, if not all, of the steps in the dosimeter manufacturing process are performed automatically. Specifically, the optical measuring of the pre- and post-exposure optical densities of the layer of radiation sensitive material (steps 106 and 118) and the computing of the calibration parameters (step 110) are performed automatically. In addition, the computed mathematical parameters may be reduced automatically to encoded form (by computer 116) and applied automatically to the dosimeters (step 122). Also, the pre-exposure optical density is automatically stored in electronically encoded form (step 108) and subsequently automatically retrieved to compute the mathematical parameters. Identification codes for the dosimeter patches are automatically generated (by position encoders 140 and computer 116) to distinguish the patches from one another and facilitate correlation of the measured optical densities with the respective patches.

The above described method for individually calibrating the dosimeters 10 is based on the realization that the radiation sensitive layers or patches 14 of the dosimeters 10 have a sufficient density range so that two incremental exposures remain within the linear range of the irradiation reaction, i.e., the change in optical density in response to irradiation. Density change between the time of the calibrating exposure during manufacture and the second exposure during use is not a problem because of the initial "zero" measurement during use.

The principles of dosimeter calibration discussed above can be applied more generally to calibrating a sensor which has an irreversible reaction when subjected to an action, wherein the reaction is progressive and cumulative and related by a known generic mathematical function to the action. The reaction of a sensor is progressive when it varies with the amount of the action to which the sensor is subjected. The reaction is cumulative when it exhibits a total reaction which is a function of the sum of all the actions to which the sensor is subjected. The method described above is generally applicable under these conditions and where the sensor material is not disabled from reacting to further action after being subjected to one or more initial actions. The calibration process described herein serves to determine specific constants of the mathematical function relating the reaction of the sensor to the applied action.

According to this generalized calibration process, the sensor is subjected to a plurality of incremental instances of the action to which the sensor is sensitive, e.g., electromagnetic radiation such as X-rays or gamma rays. Each of the incremental instances of the action have a known magnitude. A cumulative reaction of the sensor to the accumulated amount of the action is measured after each time the sensor is subjected to an instance of the action. And preferably, the condition of the sensor is measured prior to first subjecting the sensor to the action (or energy). In brief, the total number of measurements made to determine the response of the sensor to the cumulative applications of the action is equal to the number of unknown parameters in the mathematical function relating the action to the reaction of the sensor. The unknown parameters of the mathematical function are computed from the known magnitudes of the incremental applications of the action and from the measured cumulative reactions of the sensor.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for calibrating a sensor which has an irreversible reaction when subjected to an action, wherein the reaction is progressive and cumulative and related by a known generic mathematical function to the action, said mathematical function being expressed in terms of its coefficients, comprising:

subjecting the sensor to a plurality of incremental instances of the action to which the sensor is sensitive, each of said incremental instances of said action having a known magnitude;

after each time the sensor is subjected to an instance of said action, measuring a cumulative reaction of the sensor to a respectively accumulated amount of said action; and computing the values of said coefficients of said mathematical function, in accordance with the mathematical function, from the known magnitudes of said incremental instances and from the measured cumulative reactions of the sensor.

2. The method defined in claim 1 wherein said action is a form of energy.

3. The method defined in claim 2 wherein said energy is radiant energy or electromagnetic radiation.

4. The method defined in claim 3 wherein said cumulative reaction is a change in optical density of said sensor.

5. The method defined in claim 4 wherein the measuring of said cumulative reaction includes optically measuring said change in optical density.

6. The method defined in claim 1 wherein the number of incremental instances of said action is one less than a total number of coefficients of the known mathematical function.

7. The method defined in claim 6, further comprising the step, performed prior to subjecting said sensor to a first instance of said action, of measuring an initial value of a parameter of said sensor which exhibits said cumulative reaction in response to said incremental instances of said action.

* * * * *